United States Patent
Strauss et al.

(10) Patent No.: US 6,321,751 B1
(45) Date of Patent: Nov. 27, 2001

(54) CONDOM WITH SPIRAL CRISSCROSS RIBBING

(75) Inventors: Steven R. Strauss, Hillsdale; Richard D. Kline, Skillman; Jim D. Burns, Plainsboro; Michael J. Harrison, Princeton, all of NJ (US)

(73) Assignee: Carter-Wallace, Inc., New York, NY (US)

( * ) Notice: Subject to any disclaimer, the term of this patent is extended or adjusted under 35 U.S.C. 154(b) by 0 days.

(21) Appl. No.: 09/533,294

(22) Filed: Mar. 22, 2000

Related U.S. Application Data
(60) Provisional application No. 60/158,558, filed on Oct. 8, 1999.

(51) Int. Cl.[7] .................................................. A61F 6/04
(52) U.S. Cl. ........................................... 128/844; 128/918
(58) Field of Search ................................. 128/842, 844, 128/918; 604/347–353

(56) References Cited

U.S. PATENT DOCUMENTS

| | | | |
|---|---|---|---|
| D. 246,117 | 10/1977 | Okamoto | D24/99 |
| D. 246,118 * | 10/1977 | Okamoto | 128/844 |
| D. 246,119 | 10/1977 | Okamoto | D24/99 |
| D. 252,949 | 9/1979 | Okamoto | D24/99 |
| 2,586,674 | 2/1952 | Lonne | 128/294 |
| 4,798,600 | 1/1989 | Meadows | 604/347 |
| 4,852,586 | 8/1989 | Haines | 128/842 |
| 4,881,553 * | 11/1989 | Grossman | 128/844 |
| 5,109,871 | 5/1992 | Thornton | 128/844 |
| 5,176,152 | 1/1993 | Wheeler | 128/844 |
| 5,513,652 * | 5/1996 | Schwartz | 128/844 |
| 5,592,950 | 1/1997 | Kopelowicz | 128/842 |
| 5,601,092 * | 2/1997 | Miller | 128/844 |

* cited by examiner

Primary Examiner—Michael A. Brown
(74) Attorney, Agent, or Firm—Kenneth Watov; Watov & Kipnes, P.C.

(57) ABSTRACT

A condom includes a plurality of intersecting spiral ribs extending in two different directional planes along at least a portion of the surface between the open and closed ends of the condom, with each rib being oriented at an angle of about 15° to the transverse axis of the condom.

22 Claims, 13 Drawing Sheets

CONDOM WITH SPIRAL CRISSCROSS RIBBING

RELATED APPLICATION

This Application takes priority from co-pending Provisional Application Serial No. 60/158,558, filed on Oct. 8, 1999, under the same title. This Application is also related to co-pending design application Ser. No. 09/120,584, filed herewith for "Condom With Crisscross Ribbing".

FIELD OF THE INVENTION

The present invention relates generally to prophylactic devices used both for birth control and prevention of sexually transmitted disease, and more particularly to a condom with a textured surface for enhanced tactile stimulation of both the female and male partners.

BACKGROUND OF THE INVENTION

Condoms in the form of a sheath, are worn over the penis to help prevent pregnancy and/or transmission of sexually transmitted diseases such as syphilis, gonorrhea, chlamydia infections, genital herpes and AIDS, for example, during sexual intercourse. Condoms are typically composed of thin barrier membranes of latex or similar elastomeric materials for optimizing sensitivity, tactile sensation and heat transference during intercourse. Recognizing the material and thinness that condoms typically comprise, the risk of a break or tear in a condom during sexual intercourse is always a significant concern in condom design and manufacturing.

Generally, condoms are made by a dipping process, whereby an appropriately dimensioned mold or mandrel is dipped into a latex rubber emulsion, for example, formulated with various curing (vulcanizing) agents and accelerators. The mandrel, coated with the latex rubber emulsion, is withdrawn and subjected to elevated temperatures for drying and curing of the latex rubber to achieve the desired physical properties. The cured condom is then stripped from the mandrel and rolled into a toroidal configuration for packaging. The condom is donned by unrolling it down the shaft of the penis.

It is known in the art to include cross ribs or other projections along internal or external surfaces of a condom for the purpose of stimulating the male and female during sexual intercourse. The textured surface of such condoms provides increased frictional and tactual kinetics for enhancing tactile sensation and stimulation. Typically, the ribs or projections are integrally formed on a surface of the condom resulting from the use of grooves or notches etched in the surface of the mandrel during the dipping process. The design of the ribs or projections ranges from interrupted rings canted with respect to the radial plane to helical patterns of various ribbed arrangements.

A problem to be overcome in designing and manufacturing ribbed/textured condoms is to avoid breakage or tearing during use. The problem is linked to the configuration of the grooves or notches for forming the ribs or projections in the mandrel during the dipping step previously described. When a smooth mandrel is withdrawn from the latex rubber emulsion, the uncured liquid latex rubber flows downward for ideally forming a uniform coating or layer. However, as the uncured latex rubber readily flows along the surface of a notched mandrel, the grooves or notches in the mandrels interfere with the uniform flow causing potential backfill problems which can result in the formation of undesirable weak spots in the condom and nonuniformity in wall thickness.

It would therefore be a significant advance in the art of condoms to develop a textured condom which provides enhanced tactile sensation to both the male and female partner while avoiding the weak spots and the resulting failures that can be associated with prior art ribbed/textured condoms. An additional benefit of the condoms of the present invention is that these condoms are capable of being fabricated in a cost efficient and effective manner, using known conventional methods of condom production. This enables manufacturing facilities to produce the improved condoms with minimal retooling and/or changes to existing equipment.

SUMMARY OF THE INVENTION

The present invention is generally directed to a condom comprised of a continuous elastic tubular wall with a closed distal end and an open proximal end and a plurality of ribbing projections integrally formed on a surface of and extending along an area of the wall between the distal and the proximal end, the projections each having sidewalls extending a height from the outside surface.

In particular, one aspect of the present invention is directed to a condom which comprises:

a continuous elastic tubular wall including a closed distal end and an open proximal end; and a plurality of intersecting ribbing projections integrally formed on a surface of and extending along at least a portion of the area of the wall from the distal to the proximal end, said projections each having sidewalls extending a height from the surface.

In another aspect of the present invention, the condom comprises:

a continuous elastic tubular wall including a closed end and an opposing open end; and a plurality of intersecting spiral ribbing extending along two different directional planes for forming an interlocking closed micromesh pattern on a surface of said condom, said pattern extending along at least a portion of the area on a surface of said wall between the closed and open ends of said condom.

DESCRIPTION OF THE DRAWINGS

Various embodiments of the invention are described in detail below with reference to the drawings, in which like items are identified by the same reference designation, wherein.

DESCRIPTION OF THE INVENTION

The present invention is generally directed to a condom having a textured surface. The condom is fabricated with the advantage of providing enhanced tactile stimulation of the female partner and preserving the sensitivity and heat transference qualities of the condom while avoiding the weak spots and nonuniformity of condom wall thickness typically associated with prior art ribbed/textured condoms. In addition, the condoms may be fabricated easily in a cost efficient and effective manner using known conventional methods of making condoms.

Figure 1A:
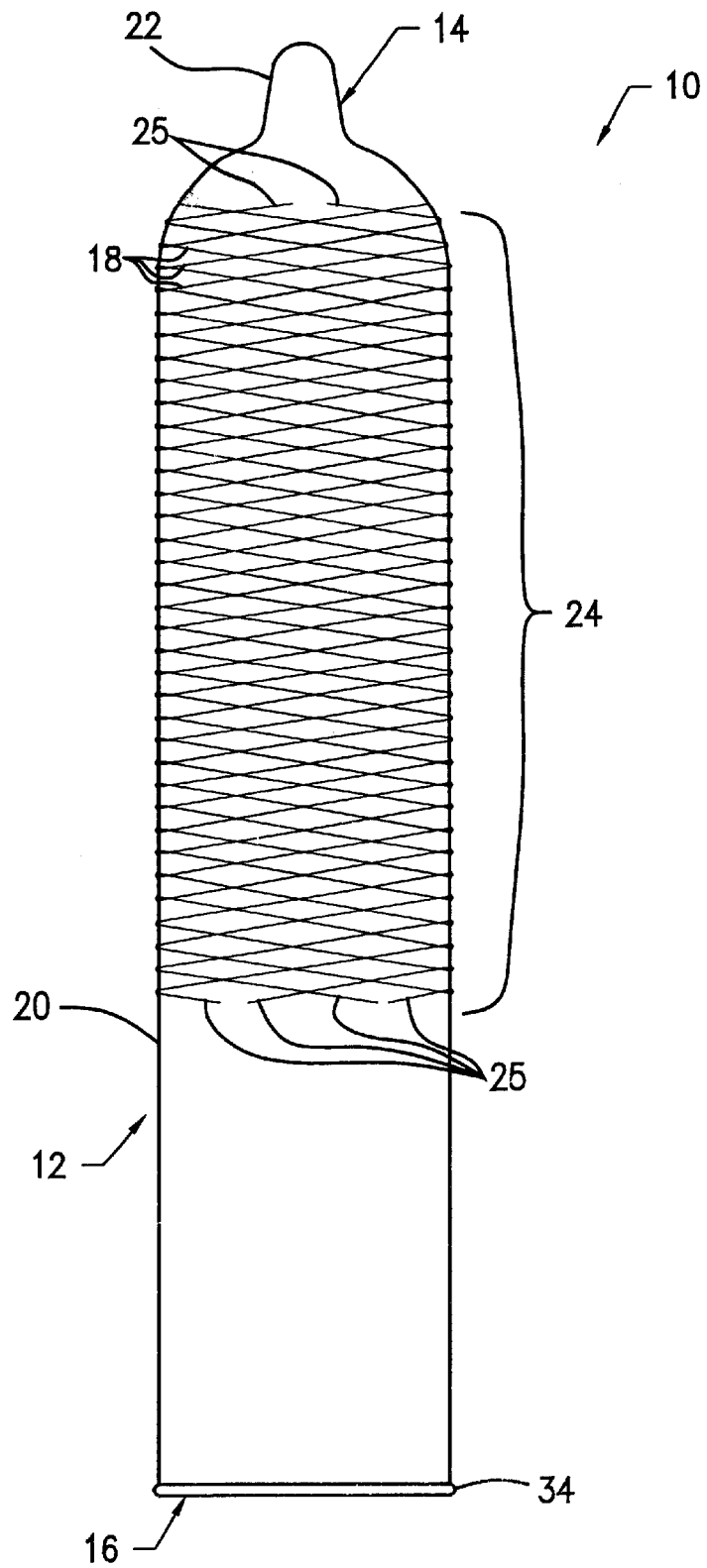
FIG. 1A is a front elevational view of a condom having a textured surface for a preferred embodiment of the invention.

Referring to FIG. 1A, a condom 10 of the present invention includes a tubular wall 12 of latex or similar elastomeric material, a closed distal end 14, an open proximal end 16 and a plurality of intersecting spiral ribs 18 extending along two different directional planes integrally formed on a surface 20 of the condom 10. The condom 10 is preferably formed of a single, homogenous prophylactically impervious, elastomeric material such as latex or polyurethane, for example. A nipple 22 may also be included at the distal end 14 for capturing ejaculated semen.

Figure 1B:
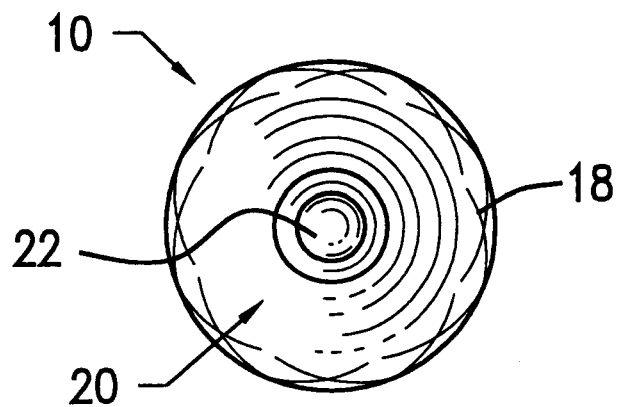
FIG. 1B is a top plan view of the condom of FIG. 1A.
Figure 1C:
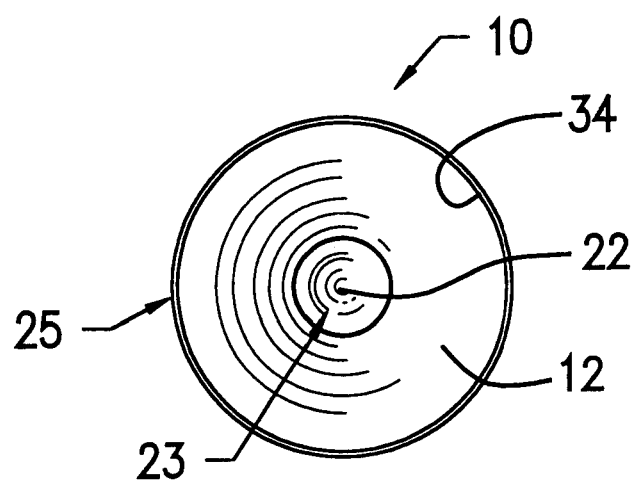
FIG. 1C is a bottom plan view of the condom of FIG. 1A.

Referring to FIG. 1B, a top plan view of the condom is shown. The outer periphery is substantially round with the nipple 22 located centrally therefrom. The spiral ribs 18 begin to extend along a surface 20 of the condom 10 at a distance from the nipple 22. Referring to FIG. 1C, a bottom plan view of the condom 10 is shown. The interior of the tubular wall 12 is smooth with a reservoir cavity 23 enclosed by the nipple 22 disposed at the end therein. A ring 34 is rolled at the open end 16 (see FIG. 1A) of the tubular wall 12 for preventing tears along its base periphery 25.

Figure 2:
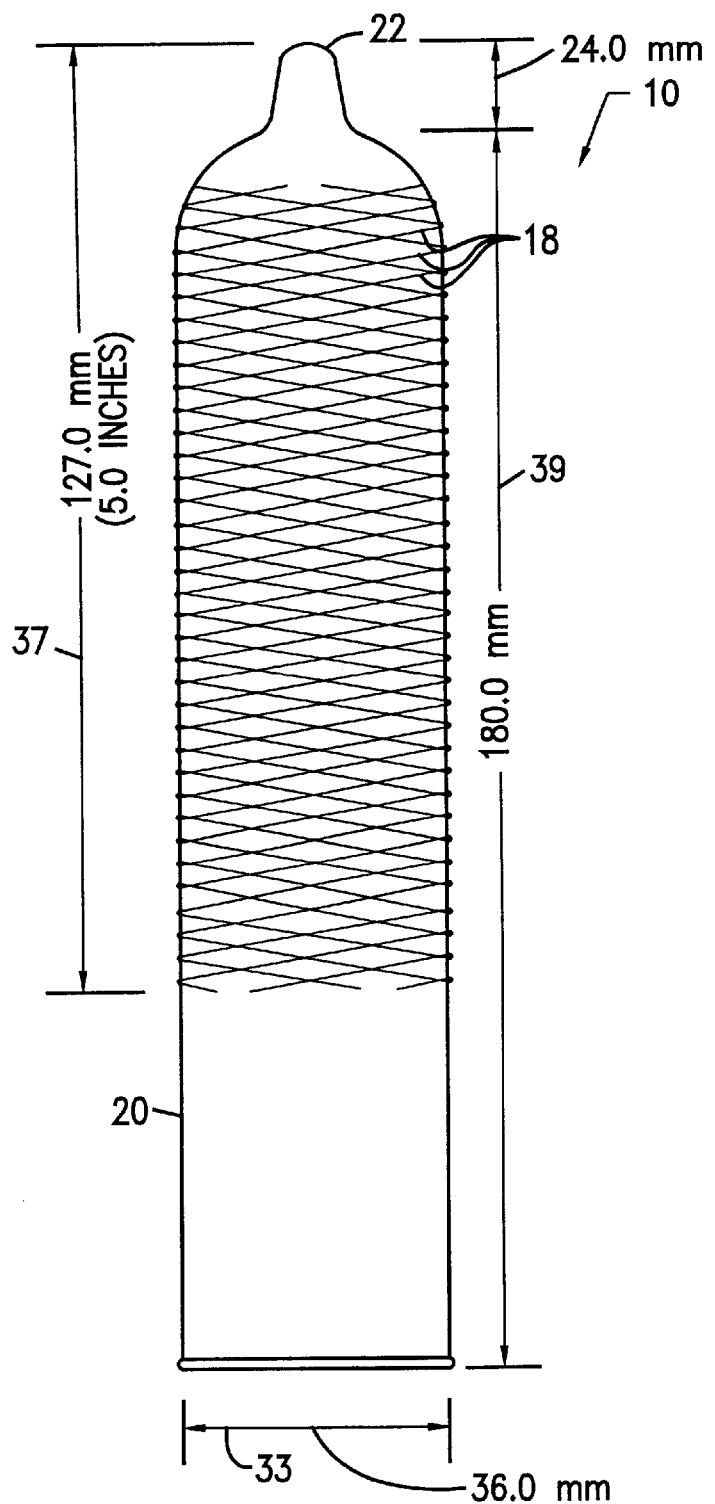
FIG. 2 is a front elevational view of the condom with size dimensions indicated.
Figure 3:
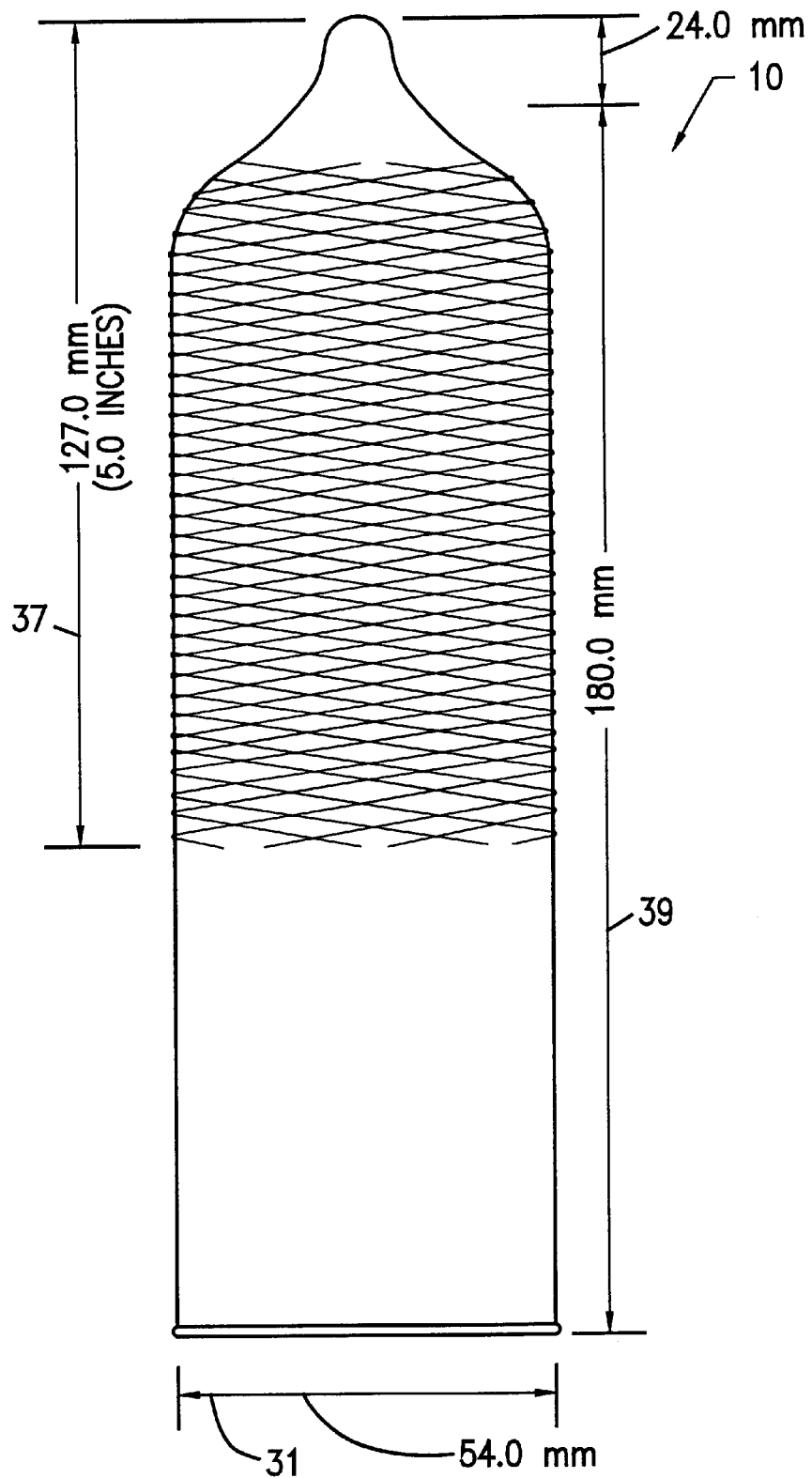
FIG. 3 is a front elevational view of the condom in a flattened condition with the associated size dimensions indicated.

The dimensions of the condom 10 are shown in more detail in FIGS. 2 and 3, respectively, for example. FIG. 2 shows the inner diameter and length of the condom 10 as indicated by arrows 33 and 39, respectively, and the preferable length of the nipple 22 and the area of the ribs 18 as indicated by arrow 37. However, it will be understood that the ribs 18 may begin and end at any point on surface 20 of the condom 10. FIG. 3 shows the same condom 10 in the flattened condition with a flat width of 54 mm as indicated by arrow 31. These dimensions are shown for illustrative purposes and are not to be construed as limiting in scope. Other sizes, dimensions and pattern area coverage may be utilized as required for making condoms of different sizes and/or shapes.

Referring again to FIG. 1A, the condom 10 includes a ribbing pattern 24 that is configured to provide stimulating pleasurable sensation and sensual excitement for both the male and female partners. Each of the ribs 18 is slightly raised above the surface 20 for increased frictional and tactual kinetics in the female during intercourse. The condom 10 utilizes the ribbing pattern 24 almost the full length of the condom 10. However, the length of the pattern 24 is not limited as such and may be varied as required. The ribs 18 are generally parallel to others of the same directional plane and uniformly spaced about the circumference of the condom 10. The spiral ribs 18 each include opposing ends 25 located in conjunction with the ends of the ribbing pattern 24. The rib ends 25 each remain open. The dimension of the ribs 18 are preferably in a range of 0.001 inch to 0.050 inch high, and more preferably 0.002 inch to 0.004 inch with a nominal height of about 0.0025 inch, from the adjacent surface of the condom 10, and in a range of 0.0001 inch to 0.050 inch in thickness.

The spiral ribs 18 which produces the ribbing pattern 24 continuously extends in either two different directional planes and intersect at various points, similar to an "X", to create an interlocking closed micromesh pattern.

The integral structure of the condom wall 12 and the ribs 18 are simultaneously provided in the dipping process. The condom 10 is formed by the dipping of a preformed stainless steel, aluminum, plastic or glass mandrel into a latex solution, in this example. The latex solution tends to adhere to the mandrel outer surface, and flows along the surface to provide a uniform latex coating which ultimately forms the condom wall 12. In order to provide the integral ribs 18, the desired rib pattern is initially cut into the mandrel corresponding to the ribbing pattern 24 of the condom 10 to be formed. Accordingly, the pattern of the mandrel recesses corresponds in a mirror image fashion to the ribbing pattern 24 of the condom 10.

Figure 4:
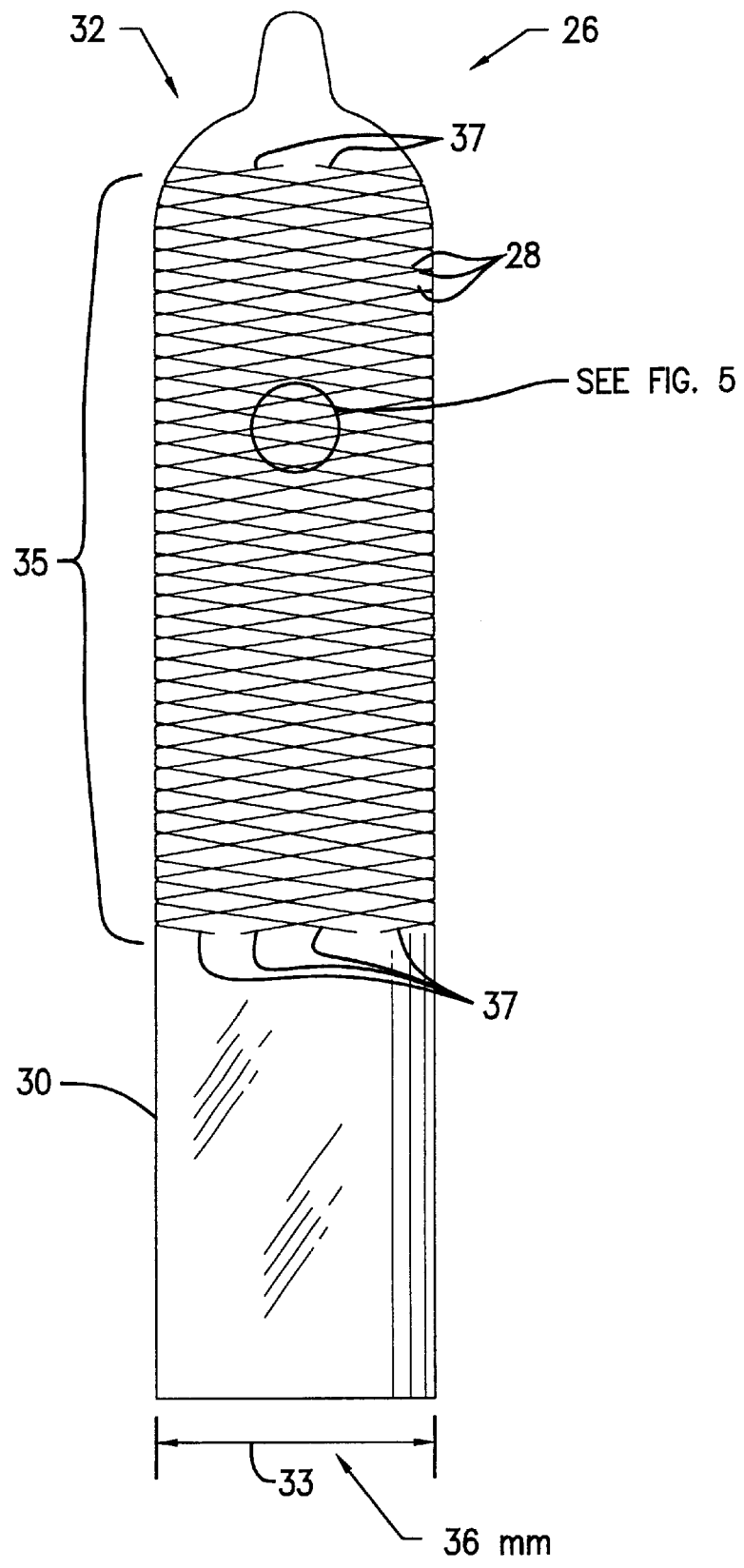
FIG. 4 is an elevational view of a mandrel utilized for the fabrication of the condom of FIG. 1.

Referring to FIG. 4, a mandrel 26 for forming the condom 10 (see FIG. 1A) of the present invention is shown. The mandrel 26 is preferably composed of glass, though other appropriate material may be utilized as well. The length of the mandrel 26 is about 360+/-3 mm, in this example. The thickness of the glass mandrel wall is about 2 mm and the outer diameter is about 36 mm. A plurality of recesses 28 are etched into an outer surface 30 for forming the ribbing pattern 24 of the condom 10. The etch depth may range from about 0.002 inch to about 0.004 inch with a nominal depth of about 0.0025 inch, and the width ranges from 0.0001 inch to 0.002 inch, for example. The recesses 28 are shaped in the form of a "V" which is generally accomplished by acid etching techniques. The shape and depth of the recesses 28 is controlled by acid strength and dwell time.

Etching of the glass mandrel 26 is accomplished by coating the glass with wax, scratching off the wax in the areas constituting the desired etch area, exposing the glass to hydrofluoric acid, regulating the acid strength and dwell time, and removing the glass mandrel 26 from the acid upon completion and neutralizing with soda and water. The wax is then removed and the glass mandrel 26 is left with the etched pattern in its outer surface 30. The etched pattern is then flame polished to remove any sharp edges produced during the etching process, to avoid weak areas in the polymeric film formed on the mandrel 26 during the dipping process. Also undercutting of the glass surface must be avoided during the etching process. The etched pattern begins at or near the distal end 32 and continues at least 5 inches along the shaft towards the other end 36. However, it must be understood that the etched pattern may begin and end anywhere along the shaft of the mandrel 26 depending on the desired condom 10 (see FIG. 1A) resultantly formed therefrom. Additionally, it is, of course, possible to provide ribs of increased thickness or height by increasing the depth of the recesses cut into the mandrel.

The immersion of the mandrel 26 with the distal end 32 first into the latex solution results in the formation of a condom 10 having a wall 12 (see FIG. 1A) including the peripherally extending ribs 18 on the surface 20. The inside or interior surface of the condom 10 is smooth as a result of the flow properties of the latex solution which evenly distribute the latex on the mandrel 26 during the dipping process. The mandrel 26 is generally dipped twice to generate the desired thickness. A ring 34 (see FIG. 1) is rolled and the latex is cured with heat. The finished condom 10 is leached, washed, and coated with powder. Prior to being foiled the condom 10 is turned inside out so that the ribs 18, which are initially molded on the interior surface, are on the outside. The condom 10 may be foiled dry, or lubricated with silicone or an appropriate anti-friction agent, and/or with a spermicidal agent for added protection against pregnancy. Note that the condom 10 can also be made from known synthetic elastomers, for example, polyurethane, and neoprene, through use of the appropriate dipping solutions and technology.

Figure 5:
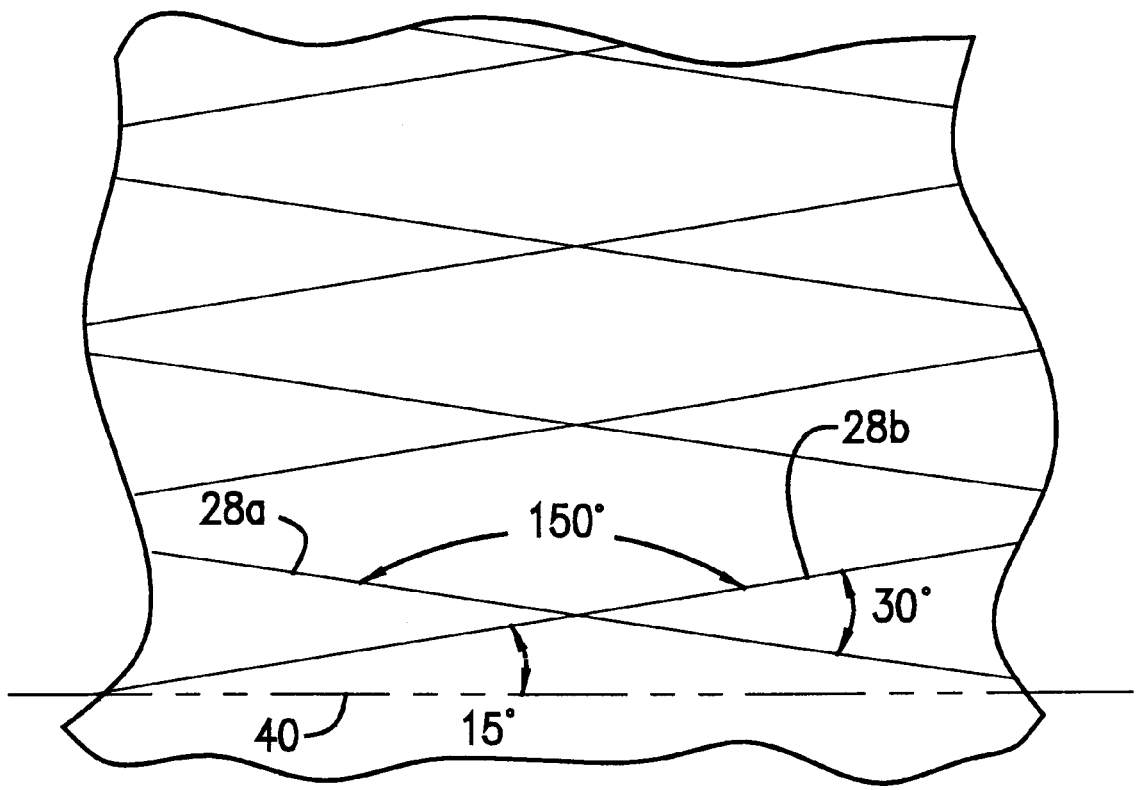
FIG. 5 is an exploded elevational view of a portion of the mandrel of FIG. 4 illustrating the angles of mandrel recesses for forming the ribs of the condom in FIG. 1.

Referring to FIG. 5, an exploded close-up view of the mandrel 26 of FIG. 4 is shown. The angles of two individual mandrel recesses 28a and 28b are shown for a preferred embodiment of the invention. Individual recess 28a extends along the surface 30 in one direction and individual recess 28b extends therealong in another direction. Each individual recess 28a, 28b are oriented at an angle in the preferred range of 0° and 90°, and more preferably at about 15° to the horizontal axis 40. In the latter angle magnitude as shown in FIG. 5, the intersections of the two individual recesses 28a,28b together form two sets of preferred angles, 30° and 150°. The pattern configuration and the associated preferred angles of the individual recesses 28a, 28b is integral to the advantage of the present invention as will be described hereinafter.

The recesses 28a and 28b in combination form a recess pattern 35 with the associated angles shown in FIGS. 4 and 5, respectively. The configuration of the recess pattern 35 minimizes the formation of weak spots in the wall 12 of the condom 10 (see FIG. 1A) during the dipping and curing process.

Typically, with prior art ribbed/textured condoms, the mandrel recesses for forming the ribbing or projections on the condom, interferes with the normal flow of uncured latex rubber over the mandrel surface generating areas of backfills and uneven distribution. This backfilling and uneven latex distribution during the dipping process eventually results in the formation weak areas in the wall of the cured condom. The resulting weak areas are susceptible to rupture and/or tearing.

In the present invention, the cross-hatched pattern and the angles of the recesses 28a and 28b of the mandrel 26 for forming the ribs 18 minimizes the flow disruption of the uncured latex rubber and provides an even distribution of latex rubber over the mandrel 26 minimizing areas of backfill for reducing or eliminating weak areas in the resulting condom 10. To further minimize the formation of weak areas, the recesses 28 further include end portions 37 (FIG. 5) for forming the rib ends 25 of the condom 10 (see FIG. 1A). The end portions 37 are arranged in a manner to minimize the backfill problem especially at the ends of the ribbing pattern 24 which are especially vulnerable to formation of weak areas in the condom wall 12.

The following embodiments as will be shown and described herein illustrate the various forms of condoms that may be used in conjunction of with the use of the ribbing pattern 24 of condom 10. The embodiments shown are not construed to be limited to such and may include variations in sizes, shapes, areas having the ribbing pattern 24, and other configurations.

Figure 6B:
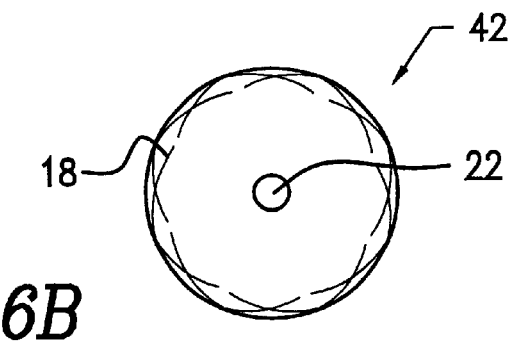
FIG. 6B is a top plan view of the condom of FIG. 6A.
Figure 6A:
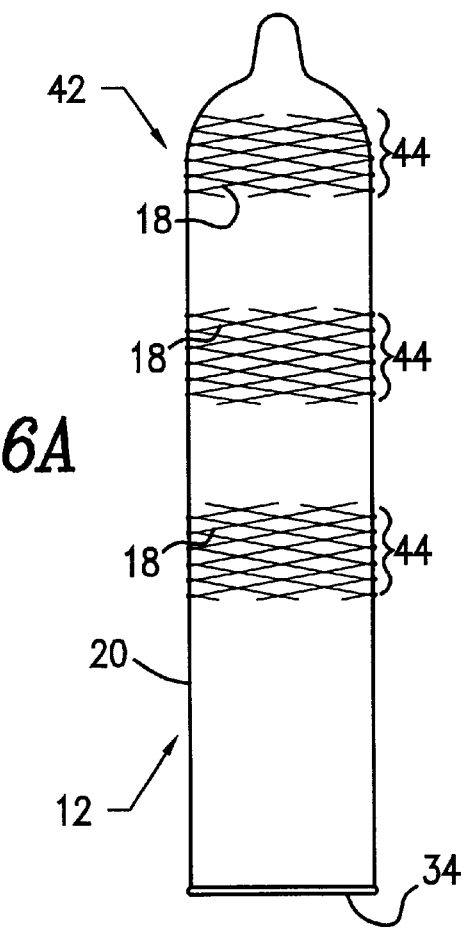
FIG. 6A is a front elevational view of a condom for a second embodiment of the invention.
Figure 6C:
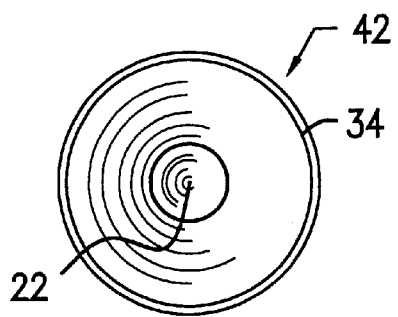
FIG. 6C is a bottom plan view of the condom of FIG. 6A.

Referring to FIG. 6A, a condom 42 is shown for a second embodiment of the invention. The shape of the condom 42 is the same as the embodiment shown in FIG. 1A. In the present embodiment, the condom 42 includes three spaced apart bands 44 of the spiral intersecting ribs 18 for forming the ribbing pattern 44 extending along portions of the surface 20 of the condom wall 12. A top plan view of the condom 42 is shown in FIG. 6B. A bottom plan view of the condom 42 is shown in FIG. 6C.

Figure 7B:
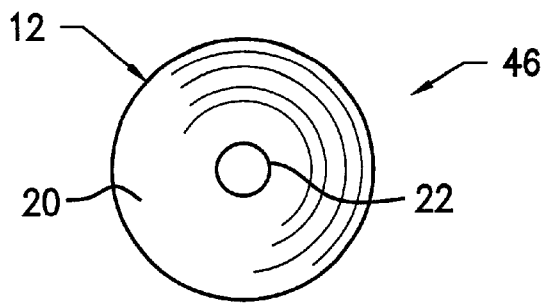
FIG. 7B is a top plan view of the condom of FIG. 7A.
Figure 7A:
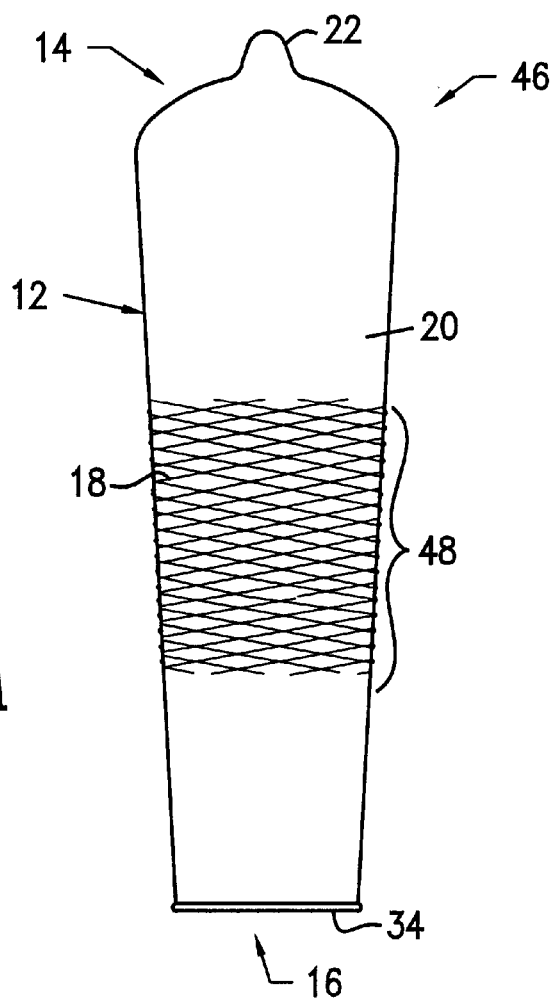
FIG. 7A is a front elevational view of a condom for a third embodiment of the invention.
Figure 7C:
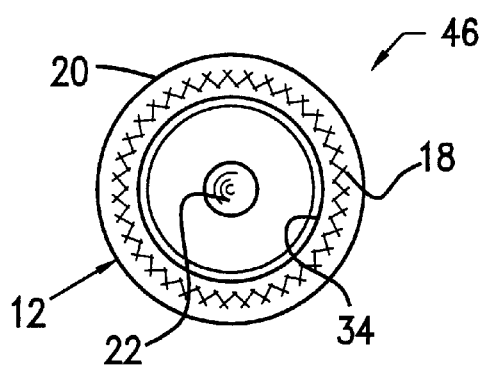
FIG. 7C is a bottom plan view of the condom of FIG. 7A.

Referring to FIG. 7A, a condom 46 is shown for a third embodiment of the invention. The condom 46 includes a baseball bat shape where the wall 12 tapers slightly from the substantially blunt closed distal end 14 down to the open proximal end 16. The condom 46 further includes a portion 48 comprised of intersecting spiral ribs 18 for forming the ribbing pattern extending along the surface 20 of the condom wall 12. A top plan view of the condom 46 is shown in FIG. 7B. A bottom plan view of the condom 46 is shown in FIG. 7C.

Figure 8B:
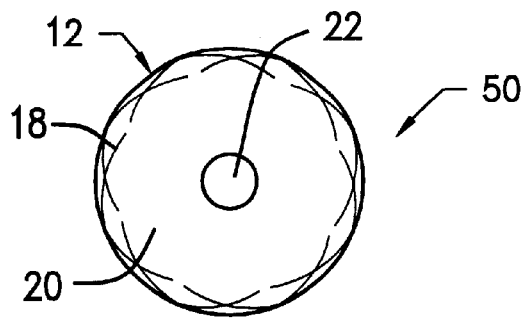
FIG. 8B is a top plan view of the condom of FIG. 8A.
Figure 8A:
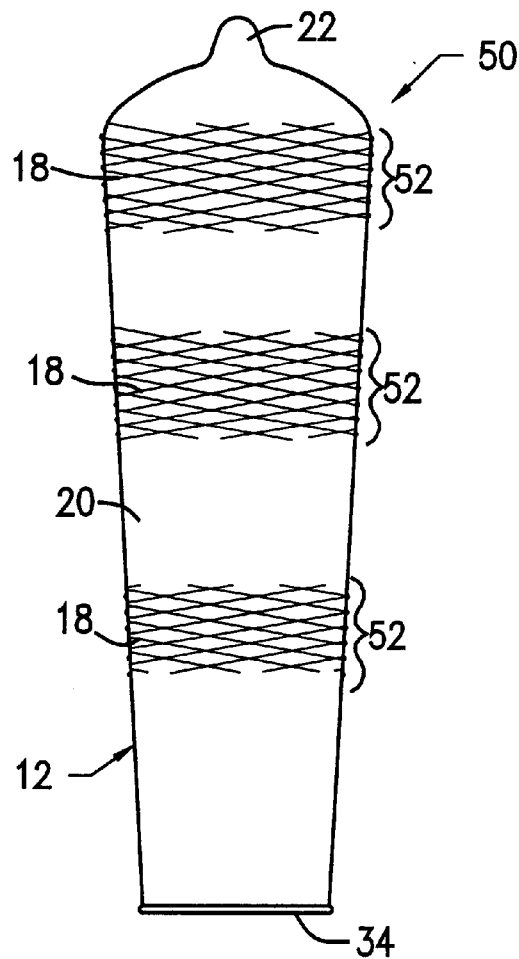
FIG. 8A is a front elevational view of a condom for a fourth embodiment of the invention.
Figure 8C:
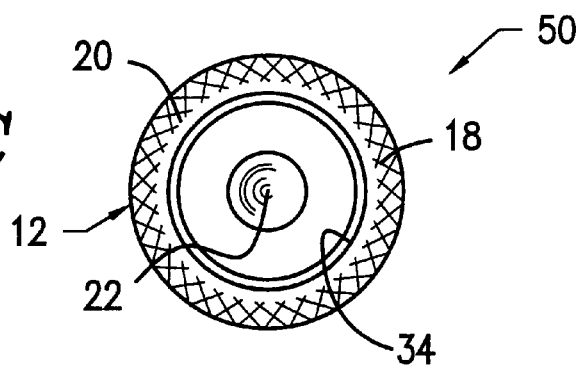
FIG. 8C is a bottom plan view of the condom of FIG. 8A.

Referring to FIG. 8A, a condom 50 is shown for a fourth embodiment of the invention. The condom 50 is very similar to the embodiment shown in FIG. 7A. However, the condom 50 includes a plurality of spaced apart bands 52 of intersecting spiral ribs 18 for forming the ribbing pattern extending along portions of the surface 20 of the condom wall 12. A top plan view of the condom 50 is shown in FIG. 8B. A bottom plan view of the condom 50 is shown in FIG. 8C.

Figure 9B:
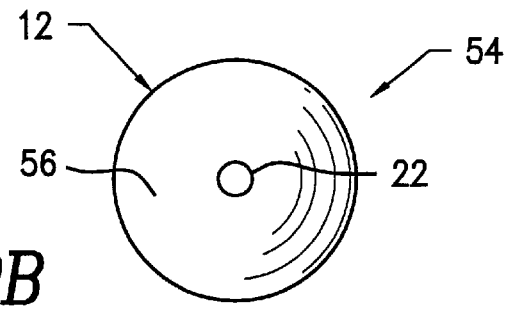
FIG. 9B is a top plan view of the condom of FIG. 9A.
Figure 9A:
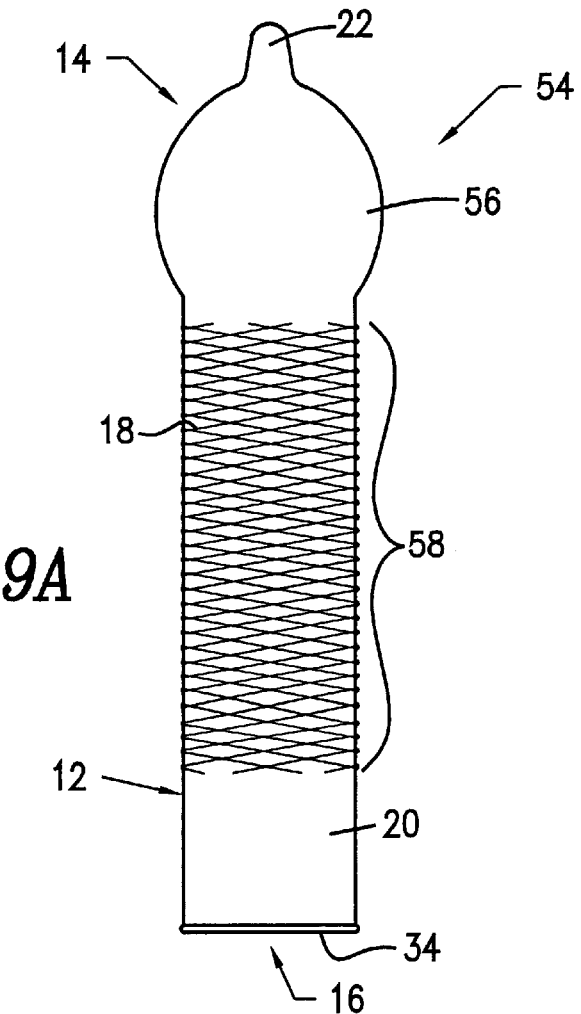
FIG. 9A is a front elevational view of a condom for a fifth embodiment of the invention.
Figure 9C:
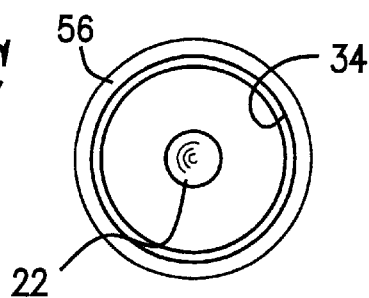
FIG. 9C is a bottom plan view of the condom of FIG. 9A.

Referring to 9A, a condom 54 is shown for a fifth embodiment of the invention. The condom 54 includes a substantially cylindrical wall 12 and a bulbous portion 56 proximate the closed distal end 14. The condom 54 further includes a textured portion 58 having the ribbing pattern extending along a section of the surface 20 of the condom 54. A top plan view of the condom 54 is shown in FIG. 9B. A bottom plan view of the condom 54 is shown in FIG. 9C.

Figure 10B:
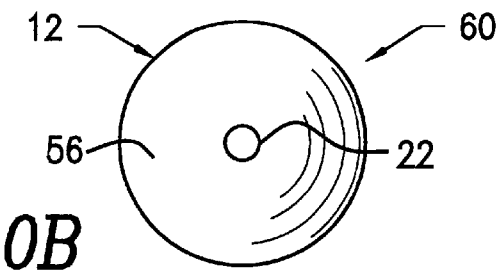
FIG. 10B is a top plan view of the condom of FIG. 10A.
Figure 10A:
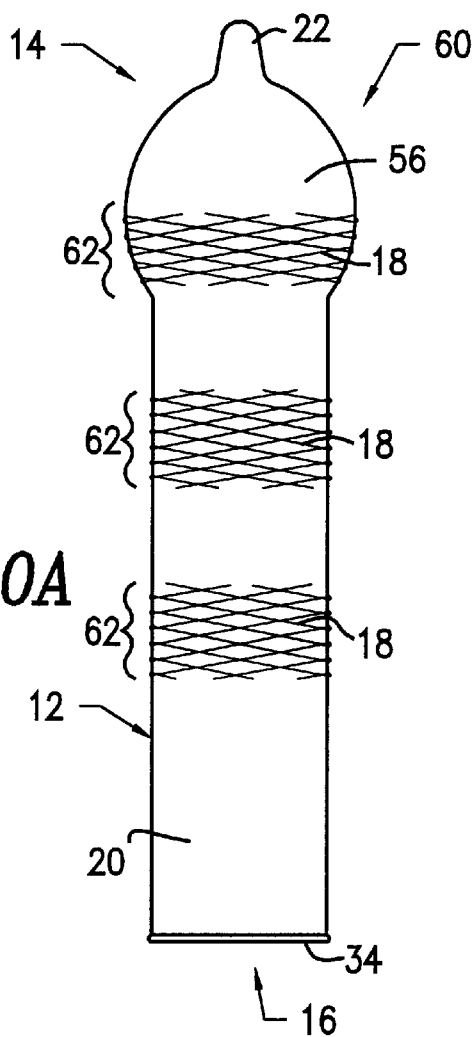
FIG. 10A is a front elevational view of a condom for a sixth embodiment of the invention.
Figure 10C:
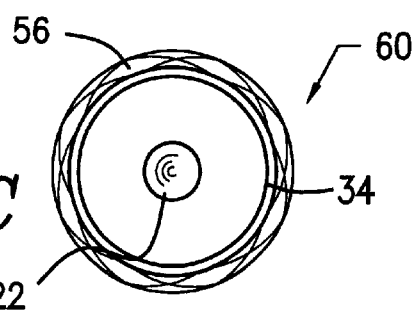
FIG. 10C is a bottom plan view of the condom of FIG. 10A.

Referring to FIG. 10A, a condom 60 is shown for a sixth embodiment of the invention. The shape of the condom 60 is the same as the previous embodiment illustrated in FIG. 9A, however, the condom 60 includes a plurality of spaced apart bands 62 of the ribbing pattern extending along portions of the surface 20 thereof. A top plan view of the condom 60 is shown in FIG. 10B. A bottom plan view of the condom 60 is shown in FIG. 10C.

Figure 11B:
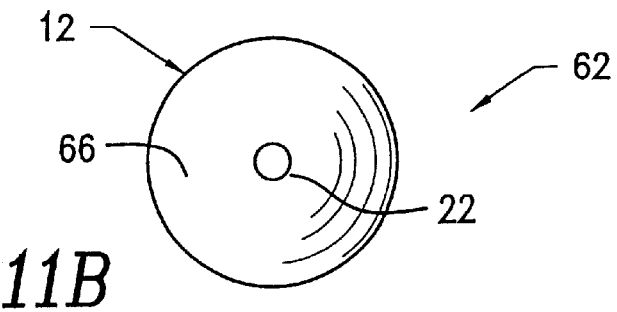
FIG. 11B is a top plan view of the condom of FIG. 11A.
Figure 11A:
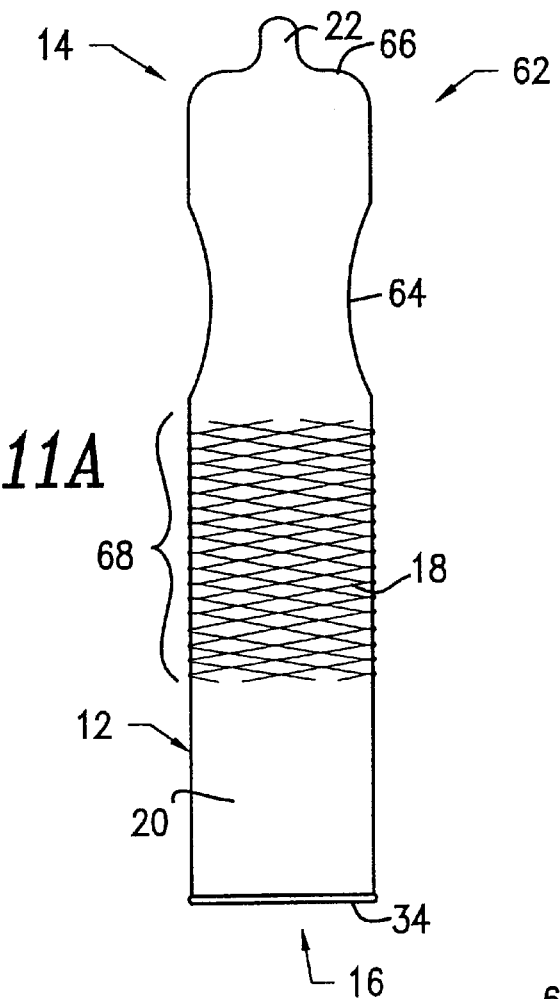
FIG. 11A is a front elevational view of a condom for a seventh embodiment of the invention.
Figure 11C:
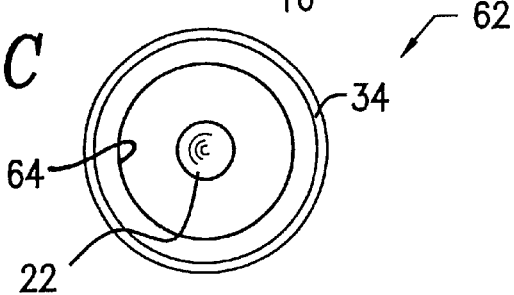
FIG. 11C is a bottom plan view of the condom of FIG. 11A.

Referring to FIG. 11A, a condom 62 is shown for a seventh embodiment of the invention. The condom 62 includes a substantially cylindrical wall 12 with an inwardly curving midportion 64 and a flattened surface 66 around the nipple 22 at the closed distal end 14. A portion 68 of the surface 20 immediately below the midportion 64 includes the intersecting spiral ribs 18 for forming the ribbing pattern. A top plan view of the condom 62 is shown in FIG. 11B. A bottom plan view of the condom 62 is shown in FIG. 11C.

Figure 12B:
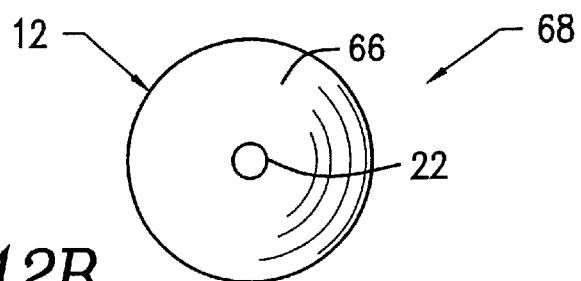
FIG. 12B is a top plan view of the condom of FIG. 12A.
Figure 12A:
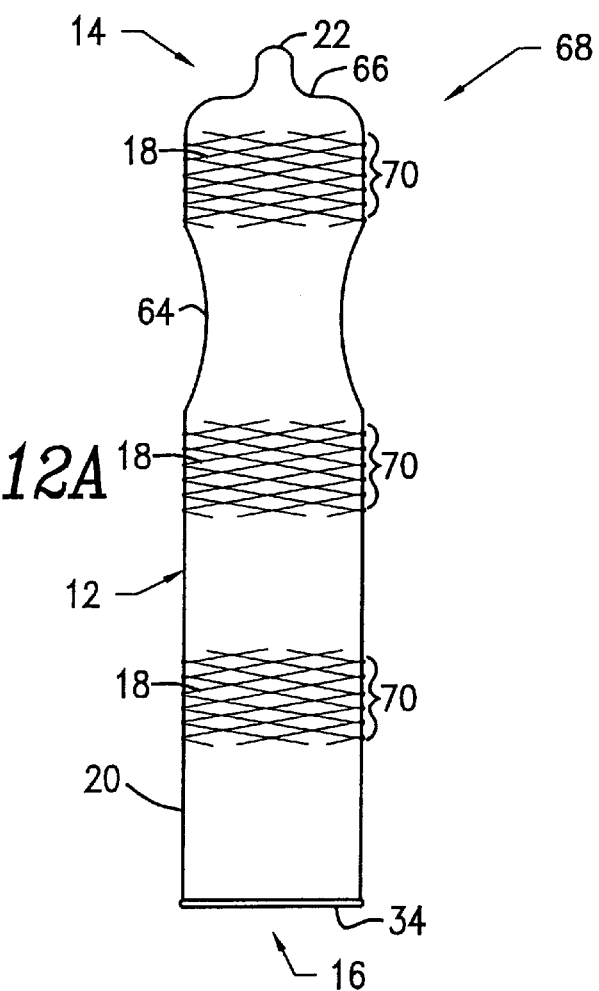
FIG. 12A is a front elevational view of a condom for an eighth embodiment of the invention.
Figure 12C:
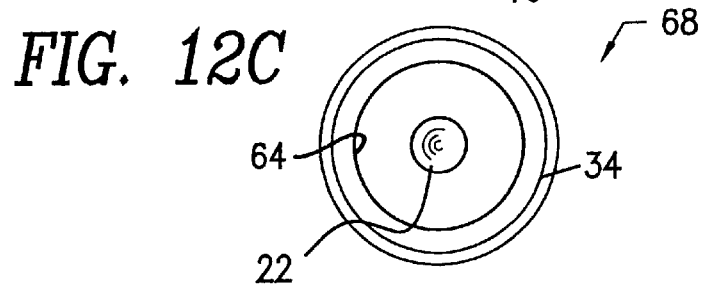
FIG. 12C is a bottom plan view of the condom of FIG. 12A.

Referring to FIG. 12A, a condom 68 is shown for an eighth embodiment of the invention. The shape of the condom 68 is the same as the previous embodiment illustrated in FIG. 11A. The condom 68 includes a plurality of spaced apart bands 70 with the intersecting ribs 18 extending along portions of the surface 20 thereof. More particularly, two of the bands 70 are located below the curving midportion 64 and the remaining band 70 extends around a portion below the flattened surface 66 at the closed distal end 14. A top plan view of the condom 68 is shown in FIG. 12B. A bottom plan view of the condom 68 is shown in FIG. 12C.

Although various embodiments of the invention have been shown and described, they are not meant to be limiting. Those of skill in the art may recognize various modifications to these embodiments, which modifications are meant to be covered by the spirit and scope of the appended claims.

What is claimed is:

1. A condom comprising:

a continuous elastic tubular wall including a closed distal end and an open proximal end; and a plurality of intersecting ribbing projections integrally formed on a surface of and extending along at least a portion of the area of the wall from the distal to the proximal end, said projections each having sidewalls extending a height from the surface;

said tubular wall, and said plurality of intersecting ribbing projections being formed together from a single, homogenous elastomeric material.

2. A condom comprising:

a continuous elastic tubular wall including a closed distal end and an opposing open proximal end; and a plurality of intersecting spiral ribbings extending along two different directional planes for forming an interlocking closed micromesh pattern on a surface of said condom, said pattern extending along at least a portion of the area on the surface of said wall between closed distal and open proximal ends of said condom;

said tubular wall, and said plurality of intersecting spiral ribbings being formed together from a single, homogenous elastomeric material.

3. The condom of claim 2, wherein each of said plurality of intersecting spiral ribbings are on the order of a range of 0.001 inch to 0.050 inch in height, and 0.0001 inch to 0.050 inch in thickness.

4. The condom of claim 2, wherein said plurality of spiral ribbings extend along its respective directional plane at an angle between 0° and 90° from the transverse axis of said condom.

5. The condom of claim 2, wherein said plurality of spiral ribbings extend along its respective directional plane at an angle of about 15° from the transverse axis of said condom.

6. The condom of claim 2, wherein said plurality of spiral ribbings begins proximate said closed distal end and terminates at about five inches therefrom.

7. The condom of claim 2, wherein said condom consists of a latex-based elastomeric material.

8. The condom of claim 2, wherein said condom consists of a synthetic elastomeric material.

9. The condom of claim 2, wherein said closed distal end further includes a nipple shaped reservoir.

10. The condom of claim 2, wherein said closed micromesh pattern extends along two or more spaced apart portions of the surface thereof.

11. The condom of claim 10, wherein said surface includes three spaced apart portions having the closed micromesh pattern.

12. The condom of claim 2, wherein the tubular wall includes a blunt closed distal end, and side portions which tapers from the closed to the opposing open end.

13. The condom of claim 12, wherein said closed micromesh pattern extends along two or more spaced apart portions of the surface thereof.

14. The condom of claim 13, wherein said surface includes three spaced apart portions having the closed micromesh pattern.

15. The condom of claim 2, wherein the distal end includes a bulbous shaped portion having a diameter greater than the adjacent portion of the tubular wall proximate the opposing open proximal end.

16. The condom of claim 15, wherein the micromesh pattern extends along a portion of the surface immediately below the bulbous shaped portion.

17. The condom of claim 15, wherein the micromesh pattern extends along two or more spaced apart portions of the surface.

18. The condom of claim 17, wherein said surface includes three spaced apart portions having the closed micromesh pattern.

19. The condom of claim 2, wherein the tubular wall includes a blunt closed distal end, and a substantially cylindrical side portions with an inwardly curving portion at a distance from the closed distal end.

20. The condom of claim 19, wherein said micromesh pattern extends along a side portion proximate said curving portion of said tubular wall.

21. The condom of claim 19, wherein said micromesh pattern extends along two or more spaced apart side portions proximate said curving portion of said tubular wall.

22. The condom of claim 21, wherein the surface includes three spaced apart side portions with said micromesh pattern.

\* \* \* \* \*